(12) United States Patent
Jin

(10) Patent No.: US 8,748,628 B2
(45) Date of Patent: Jun. 10, 2014

(54) PROCESS AND COMPOSITION OF MAKING POLYMERIZABLE RESINS CONTAINING OXAZOLIDONE

(71) Applicant: Xiaoming Jin, Middletown, DE (US)

(72) Inventor: Xiaoming Jin, Middletown, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/710,811

(22) Filed: Dec. 11, 2012

(65) Prior Publication Data

US 2013/0184467 A1 Jul. 18, 2013

Related U.S. Application Data

(63) Continuation of application No. 13/404,031, filed on Feb. 24, 2012.

(60) Provisional application No. 61/446,522, filed on Feb. 25, 2011, provisional application No. 61/467,425, filed on Mar. 25, 2011.

(51) Int. Cl.
*C07D 263/18* (2006.01)
*C08G 73/06* (2006.01)

(52) U.S. Cl.
USPC .......................................................... 548/227

(58) Field of Classification Search
None
See application file for complete search history.

(56) References Cited

U.S. PATENT DOCUMENTS

| 2005/0076848 A1* | 4/2005 | Lyngstad ...................... 119/203 |
| 2008/0076848 A1 | 3/2008 | Jin et al. |
| 2008/0076853 A1* | 3/2008 | Jin et al. ....................... 523/116 |

FOREIGN PATENT DOCUMENTS

WO 2012116268 A1 8/2012

* cited by examiner

*Primary Examiner* — Kamal Saeed

(74) *Attorney, Agent, or Firm* — Leana Levin; Douglas J. Hura; David A. Zdurne

(57) ABSTRACT

Disclosed herein are a process and composition to make polymerizable resins containing oxazolidone, in which organic acid-catalyzed and/or thermal annealing process got involved and consequently promoted a unique intramolecular transformation from a linear urethane linkage to a cyclic urethane linkage for those specifically constructed urethane resins containing α-substituted β-ketone moieties.

11 Claims, 5 Drawing Sheets

```
XJ5-160-4-2A, as-aged 22 days/45C after 50months/RT

Pulse Sequence: s2pul

Solvent: COCl3
      Ambient temperature
File: XJ5-160-4-2A-asaged22d45C-C13
Mercury-300BB "CLK-MERCURY300"

Pulse 45.6 degrees
      Acq. time 1.815 sec
      Width 18761.7 Hz
      60000 repetitions
OBSERVE C13,  75.4628108 MHz
DECOUPLE H1, 300.1118469 MHz
      Power 34 dB
      continuously on
      WALTZ-16 modulated
DATA PROCESSING
      Line broadening 1.0 Hz
FT size 131072
Total time 35 hr, 12 min, 31 sec
```

PROCESS AND COMPOSITION OF MAKING POLYMERIZABLE RESINS CONTAINING OXAZOLIDONE

This application is a continuation application of U.S. patent application Ser. No. 13/404,031, filed Feb. 24, 2012 claiming priority to U.S. Provisional Application No. 61/446,522, filed Feb. 25, 2011, and U.S. Provisional Application No. 61/467,425, filed Mar. 25, 2011.

BACKGROUND

Isocyanate is a very versatile reactive group to yield a variety of linkages (see Scheme I), which have been widely utilized in organic preparations and polymer synthesis.

Linear ployurethane is readily prepared by reacting diisocyanate and diol and polyurea would be resulted if diisocyanate reacts with diamine instead. On the other hand, when isocyanate reacts with epoxide (Scheme II), it yields an oxazolidone derivative. Oxazolidone is a five-member heterocyclic urethane, which should impart chain rigidity and excellent thermal properties to the corresponding polymers. Polymers bearing oxazolidone in both main-chain and side-chain may be synthesized in different approaches; the most convenient method is the process from isocyanate and epoxide. This process of forming oxazolidone-containing polymers depends on several factors, such as catalysts, temperature, and the type and ratio of the reactants.

It is known to prepare poly-2-oxzalidones from diepoxides and diisocyanates by using different catalysts, which include halides of the alkali and alkaline earth metals and the metals of third group of the periodic system, such as LiCl, $MgCl_2$, $FeCl_3$, $AlCl_3$, $ZnCl_2$, quarternary ammonium salts, such as $(CH_3)_4NI$ and $(C_2H_5)_4NBr$, complexes of the Lewis acid-Lewis base type, such as LiCl-HMPA, MgCl-HMPA, AlCl3-tris(2-ethylhexyl)phosphine oxide, alcoholates of the alkali metals, alkaline earth metals, such as LiOBu, NaOBu, $Mg(OPh)_2$, $Al(OPh)_3$, and metal-organic compounds of the type $ZnR_2$, $Zn(OCOR)_2$, $AlR_3$ were also used in the past.

SUMMARY

Figure 1:
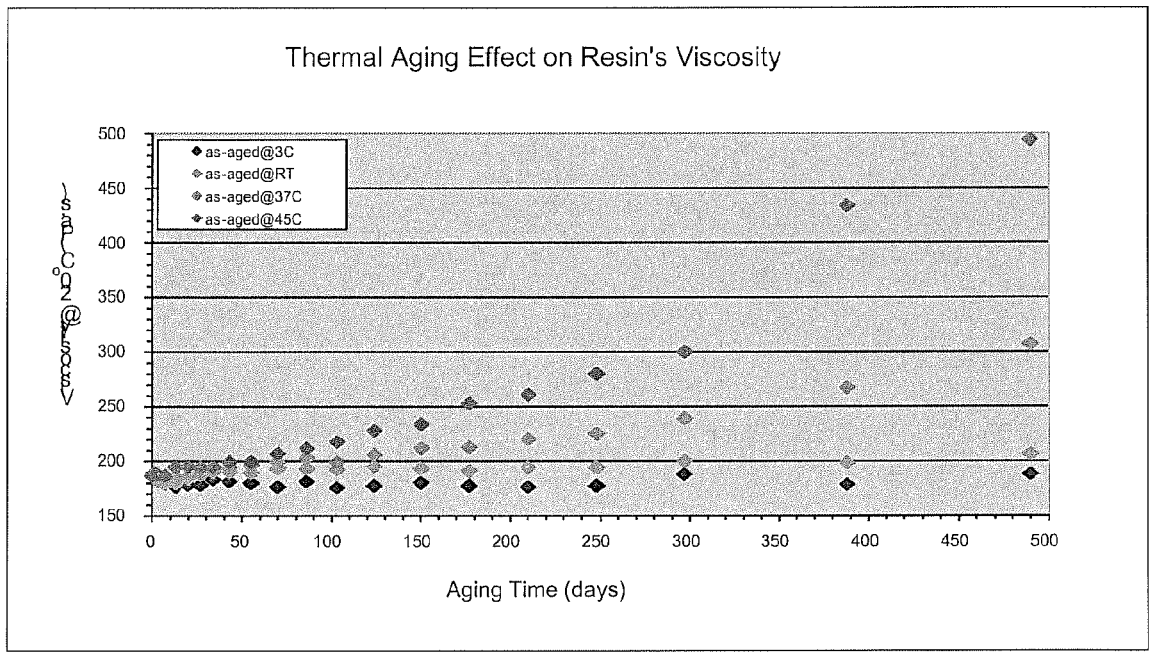
FIG. 1 demonstrates that when a conventional stress reduced resin (SDR) was thermally aged at different temperatures, ranging from 3° C., 25° C., 37° C., to 45° C., for a variable of time (up to 500 days), respectively, that the increasing viscosity of such thermally aged SDR resin becomes evident.

Disclosed herein are a process and composition to make polymerizable resins containing oxazolidone, in which organic acid-catalyzed and/or thermal annealing process got involved and consequently promoted a unique intramolecular transformation from a linear urethane linkage to a cyclic urethane linkage for those specifically constructed urethane resins containing α-substituted β-ketone moieties. Thus polymerizable resin bearing oxazolidone moiety is readily resulted under mild conditions. In addition, the increasing chain rigidity due to the oxazolidone moiety in the resulting resins offer improved thermal stability and mechanical strength. Furthermore, this disclosure also presents an effective approach to modifying the resin's viscosity without involving any forms of polymerization.

Urethane-based polymers and oligomeric resins have recently received considerable consideration, especially in biomedical and restorative dentistry. However, it remains highly desirable to further enhance the physical and mechanical performance of urethane-based materials. Obviously, oxazolidone-based urethane should be a reasonable solution to such a demand. Unfortunately, current processes of forming oxazolidone requires fairly harsh conditions such as high temperature, that is, temperatures above about 200° C., and catalysts, which also promote undesired side reactions.

In order to overcome these deficiencies of making oxazolidone derivatives, especially for those resins bearing additional polymerizable groups, such as vinyl and (meth)acrylate, the present disclosure provides mild processes for making polymerizable resins containing an oxazolidone moiety.

Specifically, disclosed herein is a polymerizble resin comprising structurally specific urethane linkages, which readily undergo intramolecular cyclization to yield oxazolidone moieties under mild processing conditions. Accordingly, the less stable groups are able to remain intact or polymerizable. Furthermore, another aspect of present disclosure is that viscosity of the disclosed polymerizable resin can be readily modified.

Scheme I: Typical Products from Isocyanate Chemistry

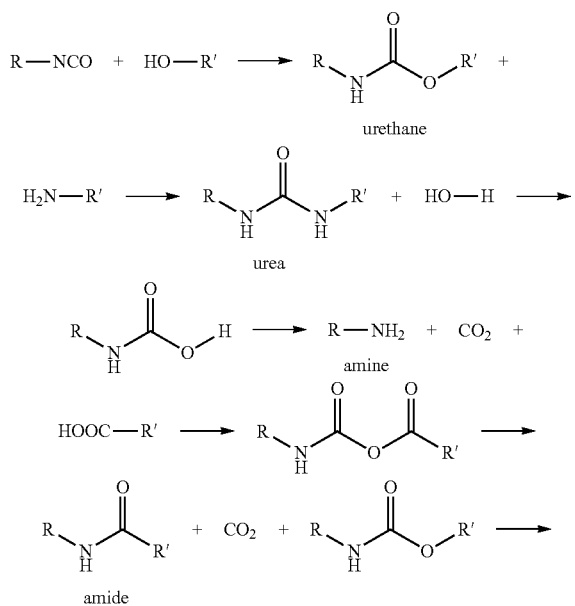

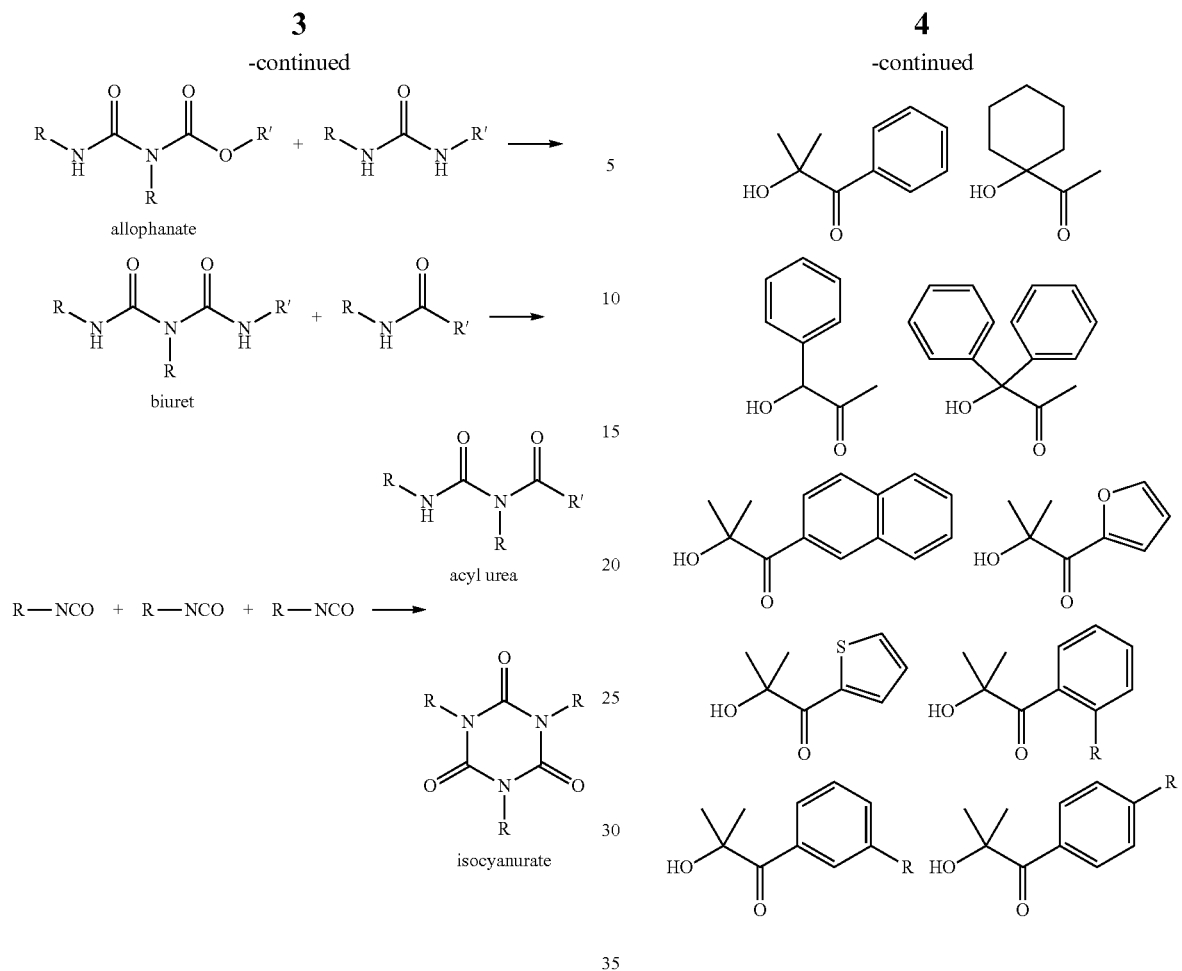
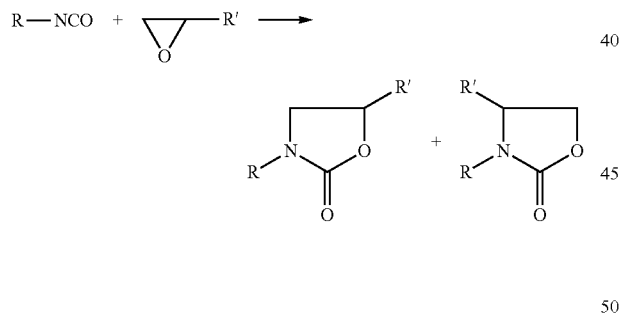
Scheme II: Oxazolidone from conventional reaction process
Scheme IIIa: Typical Structures for α-substituted β-ketone derivatives
Scheme IIIb: Typical Structures for α-disubstituted β-phenone hydroxyl derivatives
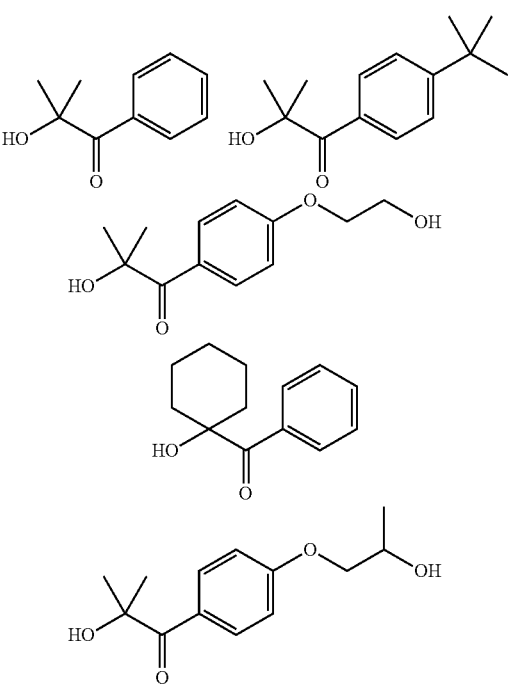

-continued

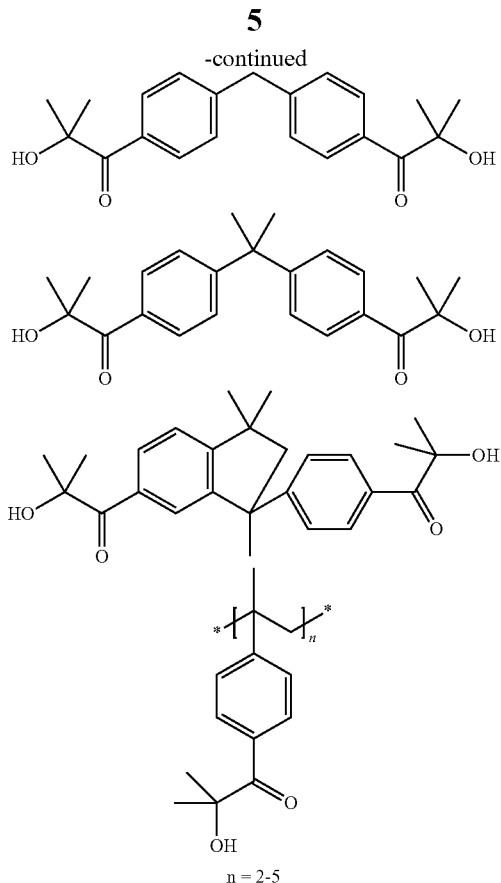

n = 2-5

DETAILED DESCRIPTION

Disclosed herein are processes to prepare a polymerizable resin that contains cyclic urethane linkage or oxazolidone moiety. The disclosed processes include at least two steps: (1) reacting at least two isocyanates, such as 1,6-hexane diisocyanate (HMDI) and a structurally specific α-disubstituted β-phenone hydroxyl compounds (as shown in Scheme IIIa and IIIb), to form a linear condensate, and (2) converting the linear urethane precursors into an oxazolidone-based resin or polymer. The conversion of the linear condensate can be induced by either thermally annealing the precursors at temperature of from about 25° C. to about 150° C., or by reacting the precursors with trace amount of inorganic or organic acids at room temperature, such as a temperature of from about 23° C. to about 27° C.

During the development of low stress resin, stress reduced resin (SDR), as described in co-owned U.S. Patent Application Publication No. 2008/0076853 and U.S. Patent Application Publication No. 2008/0076848, the entirety of which are incorporated herein by reference, it was surprisingly noted that thermal aging, or annealing, at different temperatures could cause substantial viscosity increases (as shown in FIG. 1) in the SDR resin. However, the structural analysis indicated that there was no evidence related to the involvement of the methacrylate to the viscosity building up.

Recently, in the pursuit of the process disclosed herein, it was discovered that a unique linear urethane linkage in a resin could cause the substantial viscosity increases. Specifically, the linear urethane linkage composed of an adduct of diisocyanates, such as HMDI or TMDI, and a special diol that features α-substituted β-ketone moiety and hydroxylated methacrylate provided the viscosity change.

Figure 2:
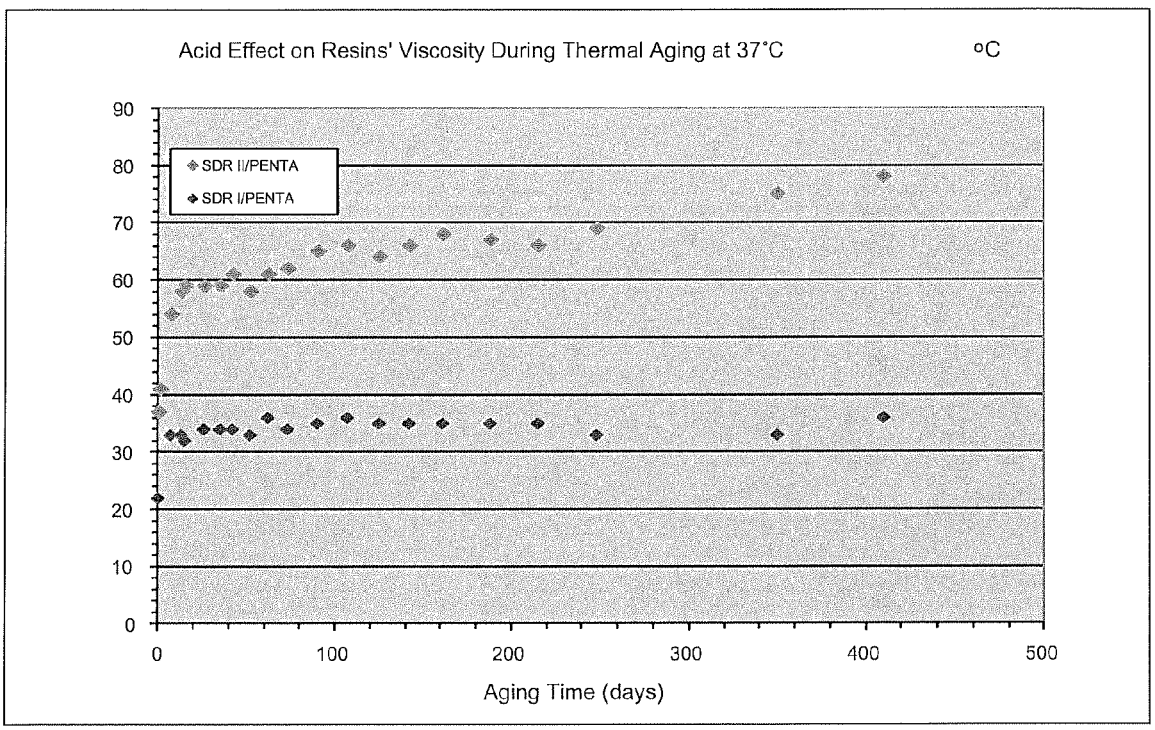
FIG. 2 demonstrates that when conventional stress reduced resin (SDR) was aged at room temperature (about 25° C.) in the presence of an acidic monomer resin, such as PENTA, for a variable of time (up to 500 days), a viscosity increase similar to the viscosity increase to thermally aged stress reduced resin (SDR) occurred. In addition.

Further structural analysis confirmed that such viscosity increase may have originated from the intramolecular cyclization of forming oxazolidone structure, as illustrated in Scheme I. It was discovered that thermally aging or annealing the resin would effectively promote such structural transformation process from linear urethane to cyclic urethane without any involvement of the (meth)acrylate groups. In addition, it was further discovered that the very same structural transformation process could also be effectively achieved in presence of acidic catalysts. For example, trace amounts of inorganic or organic acid was able to effectively accelerate such transformation process (see FIG. 2). As used herein "trace amounts" refers to from about 0.01 weight percent to about 5 weight percent of the resin composition, such as from about 0.01 weight percent to about 3 weight percent or from about 0.05 weight percent to about 1.8 weight percent of the resin composition.

An inorganic acid could be a hydrochloric acid, hydrobromic acid, hydrofluoric acid, perchloric acid sulphuric acid, nitric acid, nitrous acid, phosphoric acid, carbonic acid, or the like.

An organic acid is an organic compound with acidic properties. The most common organic acids are the carboxylic acids, associating with their carboxyl group —COOH, sulfonic acids, containing the group —SO$_2$OH, are relatively stronger acids. Some alcohols, with —OH, can also act as organic acids but they are usually very weak. Other groups can also confer acidity, such as compounds having the thiol group —SH, the enol group, and the phenol group. Examples of such organic acids include formic acid, acetic acid, propionic acid, butyric acid, valeric acid, caproic acid, enanthic acid, caprylic acid, pelargonic acid, capric acid, lauric acid, stearic acid, acrylic acid, methacrylic acid, fatty acids, amino acids, keto acids, aromatic carboxylic acids, dicarboxylic acids, tricarboxylic acids, alpha hydroxy acids. Further, phenolic acid compounds may include phenol, bisphenol, capsaicin, chavibetol, cresols, eugenol, 4-nonylphenol, picric acid (trinitrophenol), and the like.

Scheme IV: Oxazolidone from urethane transformation process

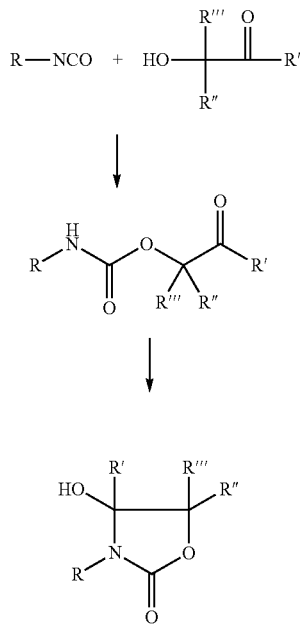

R is independently linear, branched, and cyclic alkyl alkylether, aryl(phenyl, naphthalene and their substituted) or heterocyclic rings (thiophene, pyridine, furan and their substituted), alkaryl or a combination thereof;

R' is C1-C18 of alkyl or alkylethers or cyclic alkyl or cyclic alkylethers; or aryl(phenyl, naphthalene and their substituted) or heterocyclic rings (thiophene, pyridine, furan and their substituted);

R" is hydrogen, C1-C18 of alkyl or alkylethers or cyclic alkyl or cyclic alkylethers; or aromatic rings (phenyl, naphthalene and their substituted) or heterocyclic rings (thiophene, pyridine, furan and their substituted); and R'" is hydrogen C1-C18 of alkyl or alkylethers or cyclic alkyl or cyclic alkylethers; or aromatic rings (phenyl, naphthalene and their substituted) or heterocyclic rings (thiophene, pyridine, furan and their substituted).

EXAMPLES

1. Thermal Annealing Process on a Model Compound

Figure 3A:
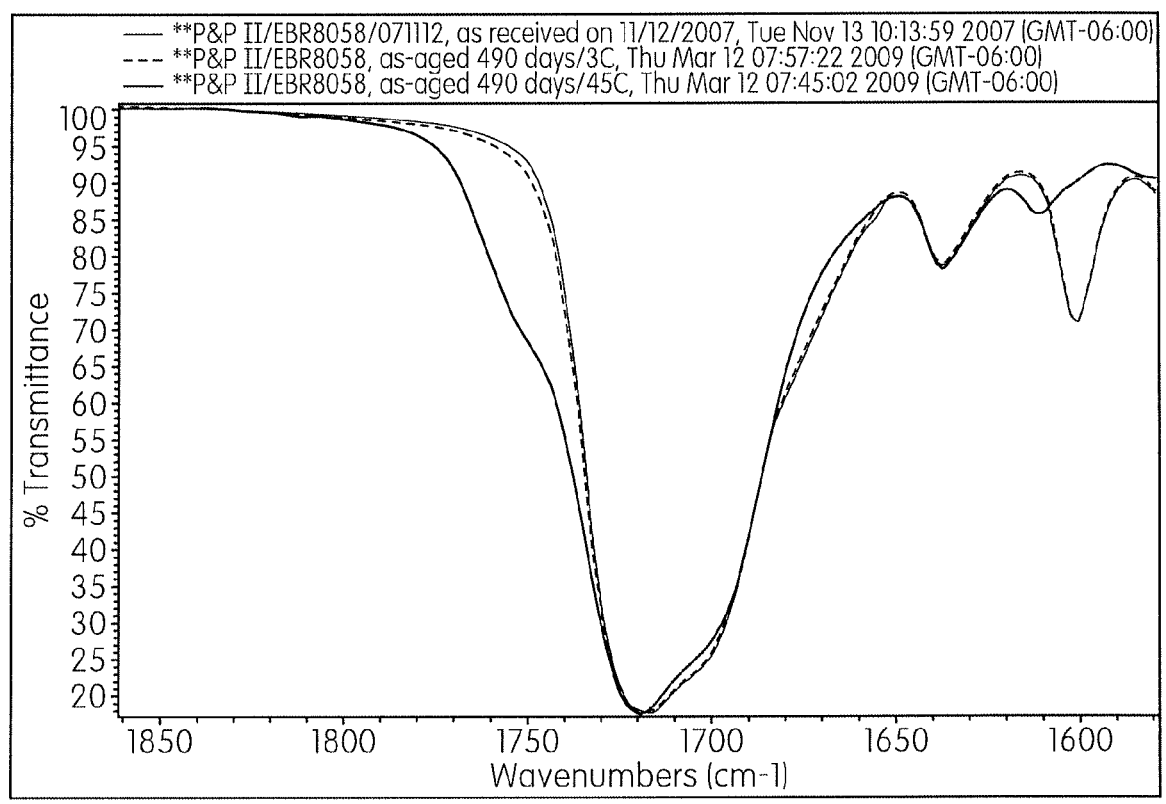
FIG. 3a demonstrates FTIR spectra for thermally transformed urethane polymerizable resin.
Figure 3B:
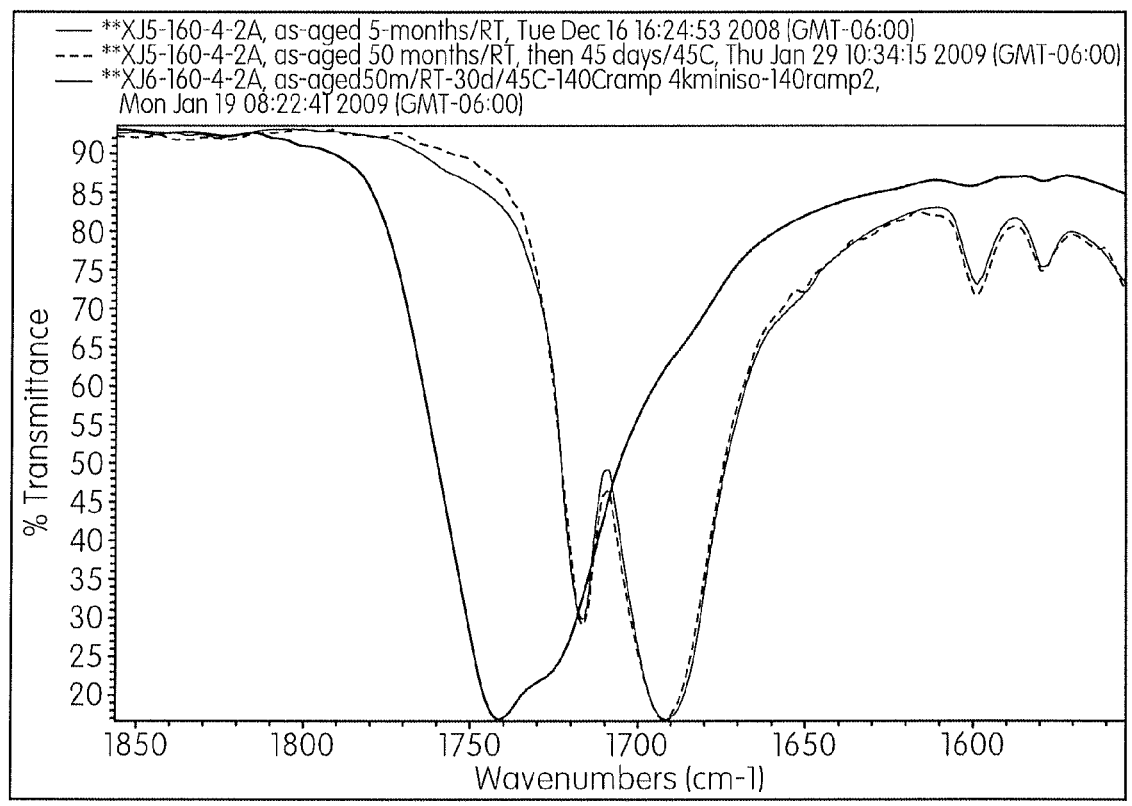
FIG. 3b demonstrates FTIR spectra of thermally transformed urethane model compound (HPN-HMDI-HPN).
Figure 4A:
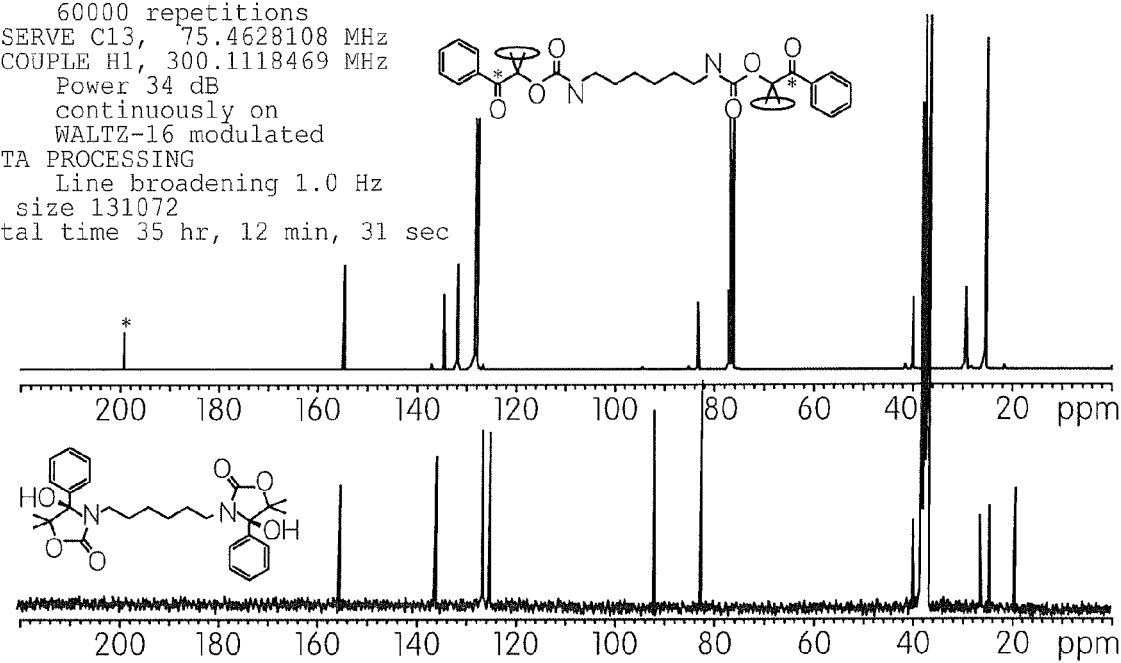
FIG. 4a demonstrates 13C NMR full spectra of thermally transformed urethane model compound (HPN-HMDI-HPN).
Figure 4B:
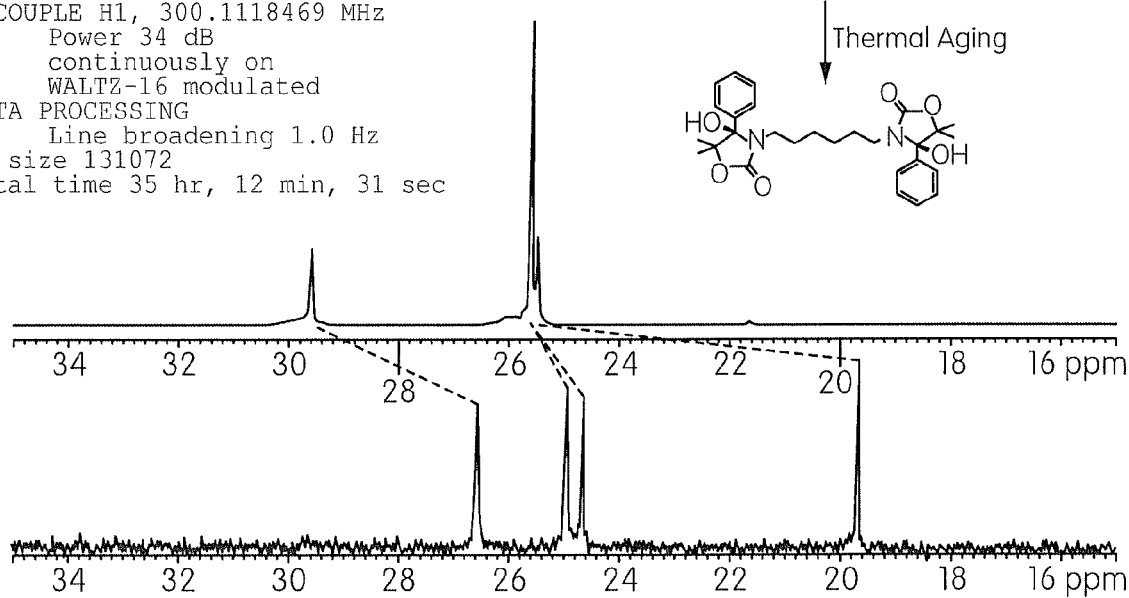
FIG. 4b demonstrates 13C NMR partial spectra of thermally transformed urethane model compound (HPN-HMDI-HPN).

A nonpolymerizable urethane compound (HPN-HMDI-HPN, as shown in Scheme V) was prepared by reactung 2-hydroxy-2-methylpropiophone (HPN) and 1,6-hexane diisocyanate (HMDI) in presence of a tin catalyst in solution. This crystalline compound was characterized by FTIR, NMR and HPLC analysis. Then it was subjected to thermal annealing, that is, the sample was heated to a temperature of from about 130° C. to about 140° C. at a rate of about 10° C./min and kept isothermal for from about 25 to about 4000 mins. Then the annealed sample was analyzed by FTIR (see FIGS. 3a and 3b) and NMR (see FIGS. 4a and 4b), respectively. There were substantial structural changes during the thermal treatment on this compound. Additional comprehensive structural analysis on the annealed compound suggested that the structural changes involved the transformation of the urethane linkage within this compound from a linear form to a cyclic corm. In other words, the two linear urethane linkages in HPN-HMDI-HPN were readily transformed into a cyclic urethane linkage or oxazolidone upon use of the thermally annealing process. Such a structure was further confirmed by HPLC analysis.

Scheme V: Transformed Urethane Model Compound (HPN-HMDI-HPN) with Oxazolidone Moiety

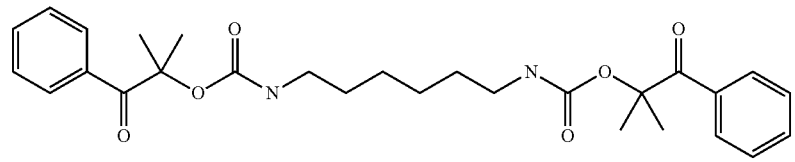

HPN-HMDI-HPN
Molecular Weight = 496.61
Molecular Formula = $C_{28}H_{36}N_2O_6$
Molecular Composition: C = 61.30%, H = 7.53%, N = 6.38%, O = 24.79%

Thermal Aging

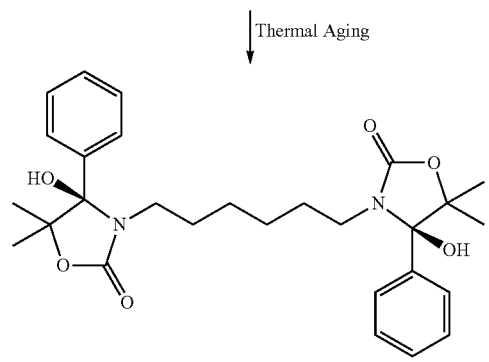

Transformed HPN-HMDI-HPN, I
Molecular Weight = 496.61
Molecular Formula = $C_{28}H_{36}N_2O_6$ 2. Acid-Catalyzed Transformation Process for a Polymerizable Resin A polymerizable urethane resin (IEM-HP-IEM, Scheme VI) was prepared by reacting 2-hydroxyl-4'-(2-hydroxyethoxy)-2-methylpropiophone (HP) and 2-isocynate-ethoxyl methacrylate (IEM) in the presence of a tin catalyst in solution. This crystalline compound was characterized by FTIR, NMR and HPLC analysis. Then this crystalline resin was mixed with small amount of acidic monomer, about 1 weight percent of the final resin composition, succinic acid mono(2-methacryloloxyethyl) ester (HEMAS) in solution for about 90 mins. Then the resulting liquid resin was analyzed by FTIR and NMR respectively. There was a substantial structural change during such a treatment of this compound. Additional comprehensive structural analysis on the liquid resin suggested that such a structural change involved a similar transformation from a linear form to a cyclic form. In addition, it was also discovered that the conventional linear urethane linkage that existed in resin remained intact, which means it does not participate in the linear to cyclic transformation in any way. Therefore we concluded such a structural transformation of a given urethane linkage is highly selective and it is strictly depends upon the intrinsic nature of the linear urethane linkage. We further identified the structural criteria is the α-substituted β-ketone moiety.

Scheme VI: Transformed Polymerizable Resin (IEM-HP-IEM) with Oxazolidone Moiety

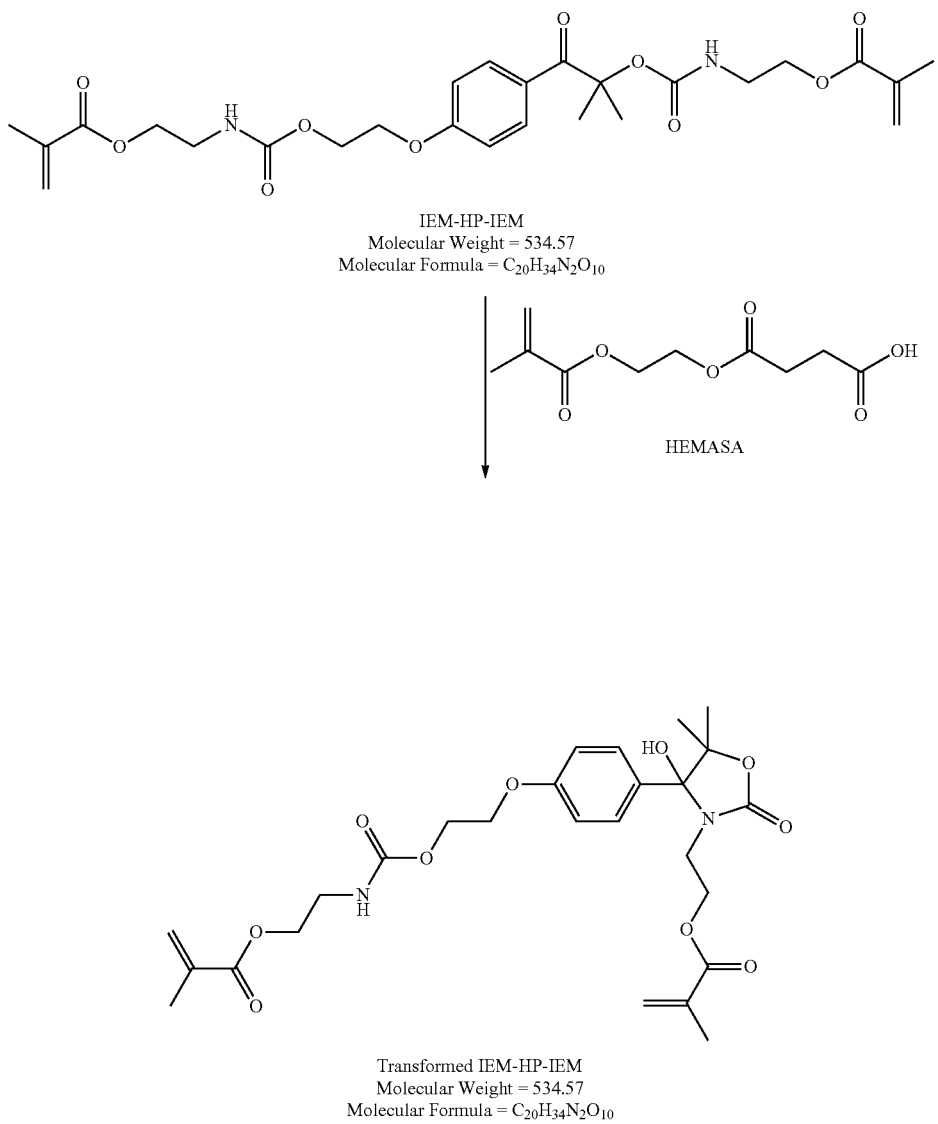

3. Thermal Annealing Process on Polymerizable Resins

As shown in Scheme VII through VIII, additional polymerizable resins containing methacrylate and/or vinyl group and the unique α-substituted β-ketone moiety in the resins were examined via thermal annealing and acid-catalyzed treatments. As showed in FIG. 1 and FIG. 2, not only temperature plays a critical role to drive these urethanes to achieve an effective intramolecular cyclization, that is forming oxazolidone, it was also discovered that a small amount of organic acid, such as methacrylic acid can accelerate such a transformation process as well, even methacrylic acid as residue in HEMA or HPMA can have this effect. Indeed the role of an acidic monomer on oxazolidone formation was confirmed by the rapid increase in viscosity for thermally aged resin in the presence of a monomer resin containing phosphoric acid, dipentaerythritol pentaacrylate monophosphate (PENTA) (see FIG. 1 and FIG. 2).

Scheme VII: Transformed SDR II Resin (HPMA-HMDI-HP-HMDI-HPMA) with Oxazolidone Moiety

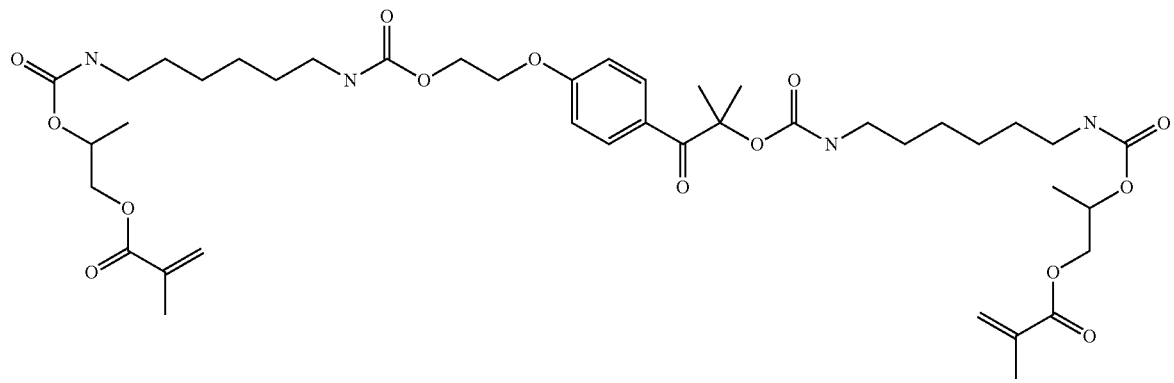

SDR II: HPMA-HMDI-HP-HMDI-HPMA
Molecular Weight = 849.00
Molecular Formula = $C_{42}H_{64}N_4O_{14}$
Molecular Composition: C = 59.99%, H = 7.47%, N = 6.77%, O = 25.78%

↓ Thermal Aging

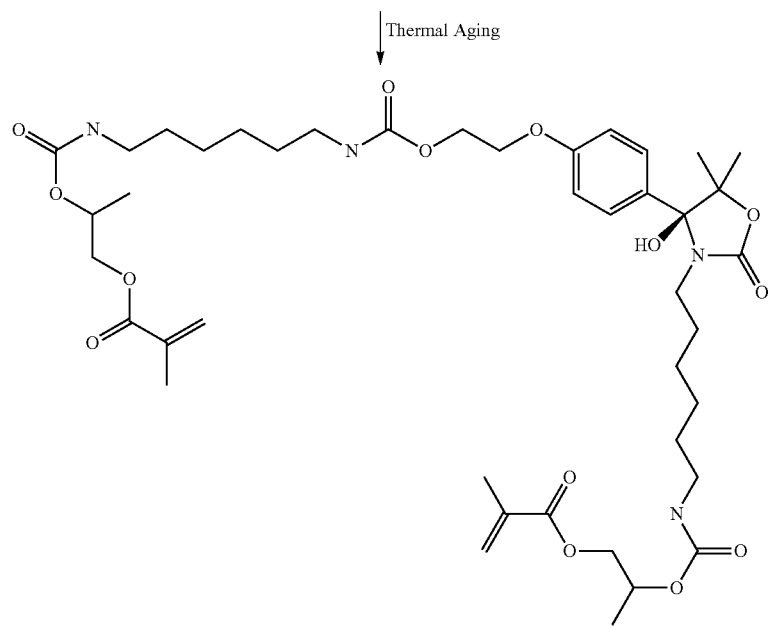

Transformed SDR II:
Molecular Weight = 849.00
Molecular Formula = $C_{42}H_{64}N_4O_{14}$
Molecular Composition: C = 59.76%, H = 7.52%, N = 6.70%, O = 26.02%

Scheme VIII: Transformed SDR V Resin (mTMI-HP-HMDI-HP-HMDI-mTMI) with Oxazolidone Moieties

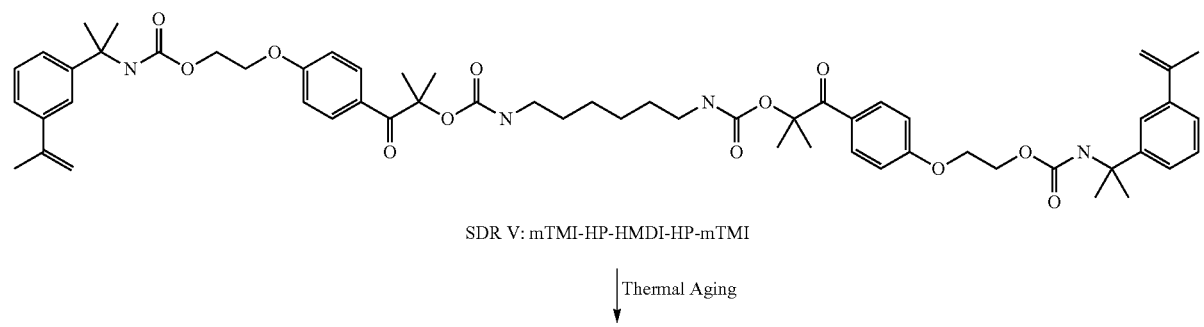

SDR V: mTMI-HP-HMDI-HP-mTMI

↓ Thermal Aging

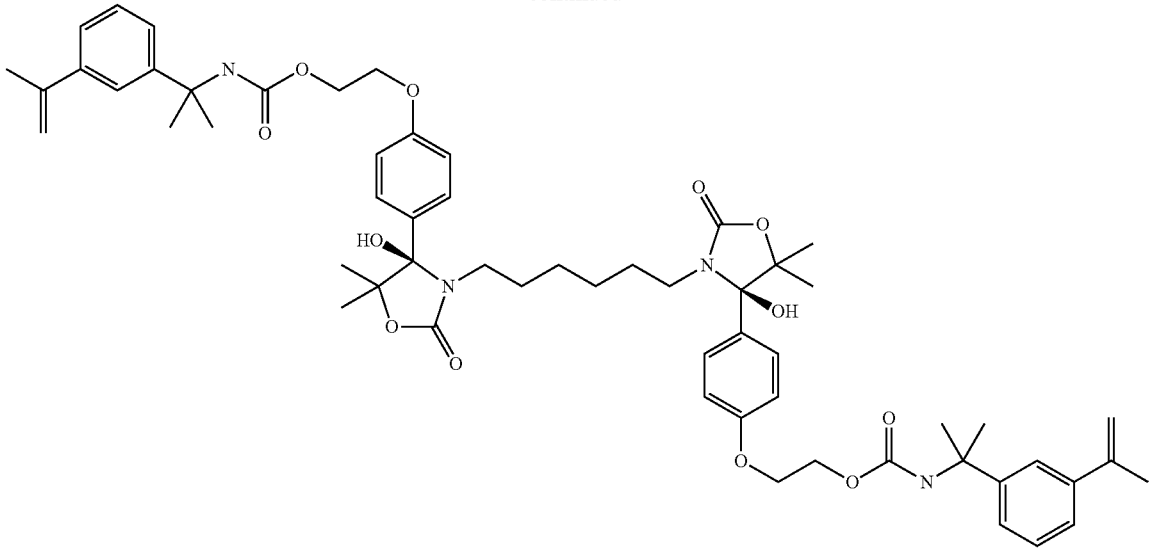

Transformed SDR V

4. Control Example

Other urethane-based polymerizable resins, such as UDMA, an adduct of TMDI and HPMA; or TPH resin, a urethane-modified BisGMA resin with HMDI, were further treated under similar conditions. For instance, a formulated TPH resin with a photoacid generator, UVI-6983 and a formulated SDR II resin with same amount of UVI-6983 were exposed UV-Vis light for induced acid and then they were thermally aged at about 37° C. for two weeks. There was no viscosity change for the TPH resin system, whereas an initial drop in viscosity was found and then it climbed back again in SDR II resin system. This indicated no structural transformation occurred in TPH resin system.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed:

1. A process, comprising:
    reacting at least two isocyanates and an α-substituted β-ketone to form a linear condensate,
    converting the linear condensate into a cyclic oxazolidone based resin or polymer,
    wherein converting the linear condensate is induced by thermally annealing the linear condensate at a temperature of from about 25° C. to about 150° C., or by reacting the linear condensate in the presence of an acid at a temperature of from about 23° C. to about 27° C.

2. The process according to claim 1, wherein the an α-substituted β-ketone has a structure of

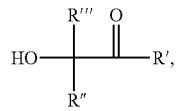

wherein R' is C1-C18 of alkyl or alkylethers or cyclic alkyl or cyclic alkylethers; or aromatic rings (phenyl, naphthalene and their substituted) or heterocyclic rings (thiophene, pyridine, furan and their substituted);

wherein R'' is hydrogen, C1-C18 of alkyl or alkylethers or cyclic alkyl or cyclic alkylethers; or aromatic rings (phenyl, naphthalene and their substituted) or heterocyclic rings (thiophene, pyridine, furan and their substituted); and wherein R''' is hydrogen, C1-C18 of alkyl or alkylethers or cyclic alkyl or cyclic alkylethers; or aromatic rings (phenyl, naphthalene and their substituted) or heterocyclic rings (thiophene, pyridine, furan and their substituted).

3. The process according to claim 2, wherein the α-substituted β-ketone is

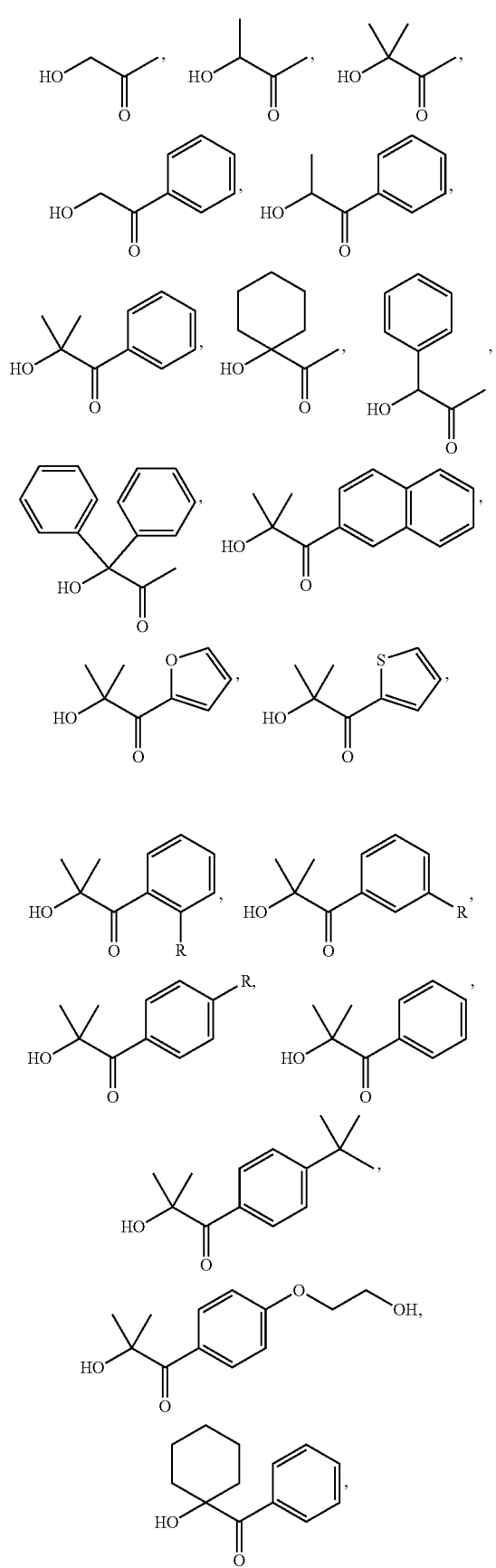

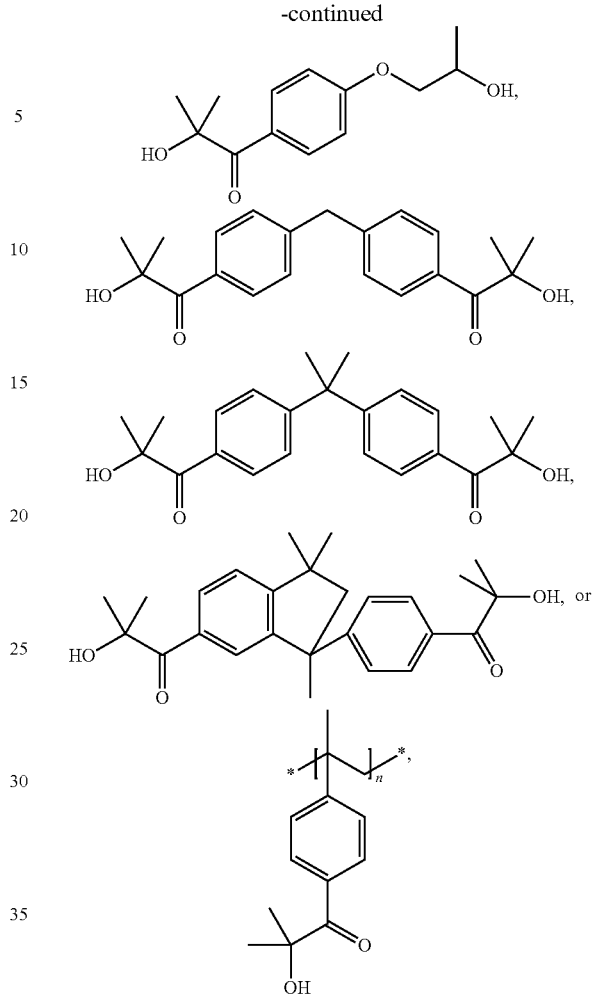

wherein n is from about 2 to about 5.

4. The process according to claim 1, wherein the linear condensate includes a linear urethane linkage.

5. The process according to claim 1, wherein the linear condensate includes polymerizable groups that remain intact even after the linear condensate is converted into the cyclic oxazolidone based resin or polymer.

6. The process according to claim 5, wherein the polymerizable groups are acrylate, methacrylate, vinyl or combinations thereof.

7. The process according to claim 1, wherein the amount of acid present during converting the linear condensate into the cyclic oxazolidone based resin or polymer is from about 0.1 weight percent to about 5 weight percent of the resin or polymer.

8. The process according to claim 1, wherein the acid is an organic acid or an inorganic acid.

9. The process according to claim 8, wherein the organic acid is a carboxylic acid, a sulfonic acids, a compound having a thiol group, a compound having an enol group, or methacrylic acid.

10. The process according to claim 9, wherein the organic acid is formic acid, acetic acid, propionic acid, butyric acid, valeric acid, caproic acid, enanthic acid, caprylic acid, pelargonic acid, capric acid, lauric acid, stearic acid, acrylic acid, methacrylic acid, fatty acids, amino acids, keto acids, an aromatic carboxylic acid, a dicarboxylic acid, a tricarboxylic acid, an alpha hydroxy acids, phenol, bisphenol, capsaicin, chavibetol, cresols, eugenol, 4-nonylphenol, or picric acid (trinitrophenol).

11. The process according to claim 8, wherein the inorganic acid is hydrochloric acid, hydrobromic acid, hydrofluoric acid, perchloric acid, sulphuric acid, nitric acid, nitrous acid, phosphoric acid, or carbonic acid.

\* \* \* \* \*